United States Patent [19]

Lewis

[11] Patent Number: 5,262,955
[45] Date of Patent: Nov. 16, 1993

[54] DUAL MODE CROSS-DIRECTIONAL MOISTURE CONTROL

[75] Inventor: Glenn R. Lewis, Lawrenceville, Ga.

[73] Assignee: Measurex Corporation, Cupertino, Calif.

[21] Appl. No.: 839,851

[22] Filed: Feb. 21, 1992

Related U.S. Application Data

[63] Continuation of Ser. No. 333,460, Apr. 5, 1989, Pat. No. 5,093,795.

[51] Int. Cl.⁵ .......................... G06F 15/46; D21F 1/02
[52] U.S. Cl. ...................................... 364/471; 364/160; 162/253; 162/258; 162/262; 162/DIG. 6
[58] Field of Search .............. 364/471, 469, 568, 148, 364/152, 160, 180; 162/198, 252, 253, 258, 262, 263, DIG. 6, DIG. 10, DIG. 11

[56] References Cited

U.S. PATENT DOCUMENTS

| | | | |
|---|---|---|---|
| 3,666,621 | 5/1972 | Adams | 364/471 X |
| 3,886,036 | 5/1975 | Dahlin | 162/DIG. 6 |
| 3,930,934 | 1/1976 | Spitz | 364/471 X |
| 4,098,641 | 7/1978 | Casey et al. | 162/DIG. 6 X |
| 4,374,703 | 2/1983 | Lebeau et al. | 162/DIG. 6 X |
| 5,093,795 | 3/1992 | Lewis | 364/471 |

Primary Examiner—Joseph Ruggiero
Attorney, Agent, or Firm—Spensley Horn Jubas & Lubitz

[57] ABSTRACT

A sheet manufacturing system having a steam profiling bar, a moisture profiling bar, a moisture sensor and a computer is disclosed. The computer is programmed to cause the correct amount of steam or water to be applied on a slice-by-slice basis based upon the moisture content profile data generated by the moisture sensor as compared against a preprogrammed, desired moisture content profile. The computer is programmed in such a way as to cause either steam or water, but not both, to be applied as needed to any given portion of each individual slice to achieve the desired moisture content profile. Thus, the combined application of both steam and water to the same portion of the sheet, and the nullifying effects thereof, are avoided, resulting in the use of less steam and less water while still providing full control over the moisture content profile with only one moisture sensor.

14 Claims, 3 Drawing Sheets

DUAL MODE CROSS-DIRECTIONAL MOISTURE CONTROL

This application is a continuation of application Ser. No. 07/333,460 filed Apr. 5, 1989, U.S. Pat. No. 5,093,795.

BACKGROUND OF THE INVENTION

The present invention relates to systems and methods for controlling a physical characteristic of a manufactured material simultaneously with the manufacturing process. More particularly, the present invention relates to a moisture control system and method which control the moisture content profile of paper sheet, in substantially discrete longitudinal segments, or "slices."

A typical paper manufacturing system has a "wet" end where its manufacturing process begins, and a "dry" end where the final product is rolled into large reels. The dry end is defined as being "downstream" from the wet end, and the wet end "upstream" from the dry end. At the wet end, a fluid, fibrous pulp mixture, referred to as "slurry," flows from a headbox onto a swiftly moving, continuous, porous belt referred to as the "wire." This forms a continuous moving sheet of slurry, referred to as the "web," which begins to lose its moisture by drainage through the pores in the wire. The web continues downstream where, prior to leaving the wire, it passes over a vacuum box which draws more moisture from the sheet. The vacuum within the vacuum box may be generated in a number of ways well known in the art; for example, by drawing air from within the vacuum box through an exhaust port with a fan.

To assist the vacuum box in drawing moisture from the web, steam may be applied to the top surface of the web by way of a "steam profiling bar" prior to the web passing over the vacuum box. By applying steam to the top surface of the web, the moisture within the web is heated and therefore its viscosity is reduced. This reduced viscosity causes the moisture to be more easily withdrawn from the web by the vacuum box. The steam profiling bar is capable of applying steam in a non-continuous manner across the width of the web. In other words, separate steam applicators within the steam profiling bar apply steam to substantially discrete, but slightly overlapping longitudinal segments, or "slices," across the width, or "cross-direction," of the web. Thus, more or less steam may be applied among the individual slices so that more or less moisture may be withdrawn from the individual slices, thereby allowing the moisture content profile in the cross-direction of the web to be tailored as desired.

Following the steam profiling bar and vacuum box, the continuous moving sheet leaves the wire and typically enters a series of opposing, felt-covered rolls which press additional moisture from the sheet. These rolls form the "press section" of the paper making machine. Following the press section, the sheet goes through a series of heated drying drums. As the sheet winds through these drying drums, it maintains physical contact with much of the circumferential surface area of each drying drum. This allows the drying drums, which are filled with pressurized steam, to heat and therefore still further dry the sheet.

Part way through this series of drying drums, the sheet passes a "moisture profiling bar." This moisture profiling bar sprays the sheet with water as desired across the cross-direction of the sheet. Similar to the steam profiling bar discussed above, this moisture profiling bar is capable of applying varying amounts of water to each slice across the cross-direction of the sheet, thereby allowing the moisture content profile in the cross-direction to be tailored as desired.

Following the moisture profiling bar, the last of the drying drums, and possibly additional processing, the sheet is rolled into a large reel. Immediately prior to being rolled up into the reel, the sheet will typically pass a scanner containing several sensors. These sensors are moved back and forth across the width of the sheet by the scanner and monitor various physical characteristics of the sheet, such as gloss, density and moisture content. Measuring the moisture content profile at this point indicates whether the paper just produced is either too wet or too dry. These measurements may be compared against the desired moisture content profile, whereupon the steam applied by the steam profiling bar and water applied by the moisture profiling bar may be adjusted appropriately.

The purpose of the steam and moisture profiling bars is to control the final moisture content profile of the manufactured paper. Typically, the desired profile will be flat. That is, it is usually desirable to have a uniform moisture content across the width and length of the sheet. Paper is sold by weight and generally has a moisture content profile specification. If the moisture content profile can be tightly controlled, the paper can be produced having the maximum moisture content, while still being within the specified limits. This results in a cheaper product, since the final product for sale contains less pulp and chemicals (expensive) and more water (inexpensive) per pound.

The prior art uses several means by which the moisture and steam profiling bars are controlled to achieve and maintain the desired moisture content. One means uses the measurements from the single scanner as discussed above to control both the moisture profiling bar and the steam profiling bar. In an attempt to avoid interaction between the moisture and steam profiling bars, i.e., applying both moisture and steam to the same portion of paper sheet, the control loops for the two profiling bars are "de-tuned." In other words, the control loops are established such that one profiling bar would respond substantially more slowly than the other profiling bar. However, this means is not entirely successful since both water and steam may still be applied to the same portions of the sheet. This is undesirable since the application of water would tend to nullify the effect of the application of the steam. Moreover, steam is relatively expensive to produce and apply, and such an expense is simply wasted when the drying effects of the steam are nullified by the subsequent application of water.

A second prior art system provides for the use of a second scanner associated with the steam profiling bar, whereby each of the profiling bars would thus have its own dedicated scanner. This second scanner would be located at a point between the steam profiling bar and the moisture profiling bar. Each scanner would independently control its own profiling bar. This configuration, however, also may result in the application of both water and steam to the same slice. This is undesirable for the reasons stated above, and moreover, requires the added expense and maintenance costs of a second scanner.

SUMMARY OF THE INVENTION

The present invention may operate with the typical paper manufacturing system, as described above, which includes a steam profiling bar, a moisture profiling bar, and a single cross-directional scanner with a sensor(s) for moisture content profile measurements. The results of the moisture content profile measurements taken by the scanner's sensor are provided to the central process control computer for the paper manufacturing machine. This computer is preprogrammed to determine the moisture content of each slice based on these measurements. This measured moisture content profile is then compared to a desired moisture content profile (typically uniform, or "flat") which was previously programmed into the computer. The computer then controls the moisture content of each slice by controlling the steam profiling bar and the moisture profiling bar as follows: if a slice is too dry, the steam applied thereto, if any, is decreased. If after another moisture measurement by the scanner the slice is still too dry, the steam applied thereto is further decreased. This continues until steam is no longer being applied to the slice. If then the slice is still too dry, the computer instructs the moisture profiling bar to begin applying water to that particular slice. If necessary, this application of water is increased until the slice reaches a desired moisture content.

Conversely, if a slice is too wet, the moisture profiling bar is instructed to decrease its application of water to that slice, if any. If, after another moisture measurement by the scanner the slice is still too wet, the application of water is further reduced. This action continues until water is no longer being applied, whereupon if the slice is still too wet, the steam profiling bar is instructed to begin applying steam. This application of steam is increased until the slice achieves the desired moisture content.

Thus, either steam or water, but not both, is applied to any given portion of a given slice. The present invention therefore provides the advantages of requiring only one cross-directional scanner and moisture sensor, and requiring less steam and water since only steam or water, not both, is applied to any given portion of a given slice of the sheet.

DETAILED DESCRIPTION OF THE PREFERRED EMBODIMENT

Figure 1:
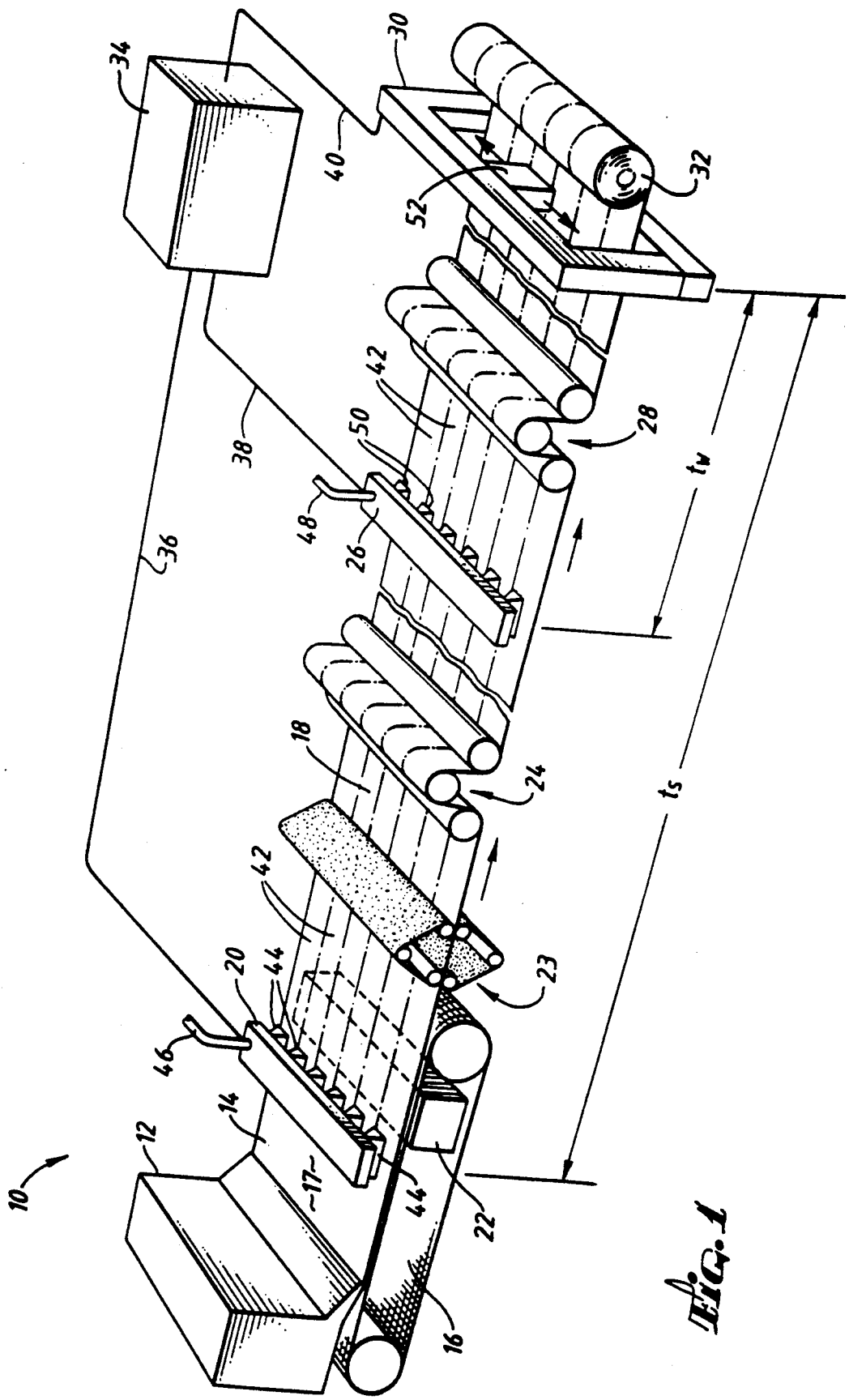
FIG. 1 is a perspective view illustrating the major components in a typical paper manufacturing system as configured for a preferred embodiment of the present invention.

FIG. 1 illustrates perspectively the major components of a typical paper manufacturing system 10 as configured for a preferred embodiment of the present invention. Upon exiting the headbox 12, the slurry 14 impinges upon the wire 16 and begins to travel downstream. Before leaving the wire 16, the web 17 passes beneath a steam profiling bar 20 and over a vacuum box 22. The web 17 leaves the wire 16 as paper 18 and enters the press section 23 and a first set of drying drums 24. Further downstream, the paper 18 passes beneath a moisture profiling bar 26 before entering the last set of drying drums 28. Finally, the paper passes through a scanning assembly 30 and is rolled up into a reel 32. A central process control computer 34 controls application of steam by the steam profiling bar 20, the application of water by the moisture profiling bar 26 and the scanning assembly 30 via control cables 36, 38, 40.

At the wet end, as the web 17 nears the end of the wire 16 and passes beneath the steam profiling bar 20, steam is applied to the individual slices 42 by way of separate steam applicators 44. The steam applicators 44 may be uniformly spaced, individually controllable steam valves (not shown) mounted on a common steam conduit, and may be actuated by electromagnetic, pneumatic, hydraulic or mechanical means (not shown). The steam profiling bar 20 receives its steam by way of a steam conduit 46 from a source of steam, such as a boiler (not shown). The application of the steam causes the moisture within the web 17 to become warmer and therefore have lower viscocity. This allows more of the moisture within the web 17 to be withdrawn by the vacuum created by the vacuum box 22 below. The separate steam applicators 44 are capable of applying selectably varying amounts of steam to each slice 42 and are controlled individually by the computer 34 by way of a control cable 36 and associated electromechanical transducers (not shown).

Further downstream between the first set of drying drums 24 and he last set of drying drums 28, the paper 18 passes beneath a moisture profiling bar 26. The moisture profiling bar 26 receives its water by way of a water conduit 48 and applies water to the individual slices 42 by way of separate water spray applicators 50. The water applicators 50 may be uniformly spaced, individually controllable water spray valves (not shown) mounted on a common water conduit, and may be actuated by electromagnetic, pneumatic, hydraulic or mechanical means (not shown). Similar to the steam applicators 44, these water applicators 50 are capable of applying selectably varying amounts of water to each slice 42 and are individually controlled by the computer 34 by way of a control cable 38 and associated electromechanical transducers (not shown).

At the dry end, the scanning assembly 30 with its scanning head 52 monitors the paper on a slice-by-slice 42 basis, by scanning back and forth in the cross-direction. The data obtained by this cross-directional scanning results in a "moisture content profile" measurement which is transmitted to the computer 34 by way of a cable 40.

In this preferred embodiment, the computer 34 is programmed to analyze the moisture content profile data obtained by the scanning assembly 30 and determine whether any slices 42 are either too dry or too wet. If a given slice 42 is too dry, either less steam or more water must be applied. If the slice 42 is too wet, either more steam or less water must be applied.

The operation of the preferred embodiment of the system 10 of the present invention, as depicted in FIG. 1, is as follows: the steam and water outputs of the steam profiling bar 20 and moisture profiling bar 26, respectively, are preset to some value by the computer 34. This preset value may be zero or some minimal value of either steam or water, as desired. The moisture content profile data gathered by the scanning assembly 30 is then analyzed. The computer 34 then determines whether each slice 42 is either too dry or too wet, as compared to a preprogrammed, desired moisture content profile. I a slice 42 is too dry, either less steam or more water must be applied to that slice 42. Therefore, the computer 34 first checks to see if steam is being applied to that slice 42 via its associated steam applicator 44. If steam is being applied, the computer 34 commands the steam profiling bar 20 to decrease, by a predetermined incremental amount, the amount of steam being applied by the particular steam applicator 44 associated with that slice 42. After a time period of "$t_s$" seconds (defined below), the computer re-analyzes the moisture data for that slice 42. If it is still too dry, the foregoing process is repeated until steam is no longer being applied to that slice 42. If however, the slice 42 is too dry but no steam is being applied to that slice 42, or is no longer being applied to that slice 42, the computer 34 then commands the moisture profiling bar 26 to begin applying water to that slice 42, or increase the amount of water if it is already being applied to that slice 42, by a predetermined incremental amount, via the water applicator 50 associated with that slice 42. Following a time period of "$t_w$" seconds (defined below), the moisture data for that slice 42 is re-analyzed by the computer 34 to determine whether additional water needs to be applied to that slice 42 by the moisture profiling bar 26 via its associated water applicator 50. If more water is required, the latter foregoing process is repeated.

If, on the other hand, a slice 42 is not too dry but is instead too wet, the computer 34 first checks to see whether water is being applied to that slice 42 via its associated water applicator 50. If so, the computer 34 commands the moisture profiling bar 26 to decrease, by a predetermined incremental amount, the amount of water being applied by the particular water applicator 50 associated with that slice 42. Following a time period of $t_w$ seconds, the moisture data for that slice is re-analyzed by the computer 34. If the slice 42 is still too wet, the foregoing process is repeated, until water is no longer being applied to that slice 42. If however, the slice 42 is too wet but no water is being applied to that slice 42, or is no longer being applied to that slice 42, the computer 34 commands the steam profiling bar 20 to begin applying steam to that slice 42, or increase the amount of steam if it is already being applied to that slice 42, by a predetermined incremental amount, via the steam applicator 44 associated with that slice 42. Following a time period of $t_s$ seconds, the moisture data for that slice 42 is re-analyzed by the central computer 34. If the slice 42 is still too wet, the latter foregoing process is repeated.

The predetermined incremental amounts of changes in applied steam and water, discussed above, are based upon a priori knowledge of the desired moisture content profile and the effective resolutions, i.e., the smallest selectable variations in output levels, of the individual steam applicators 44 and water applicators 50, respectively. For example, if the acceptable moisture content profile allows for only small variations in sheet moisture, then the applicators' individual resolutions should be high, i.e., they should provide small selectable variations in steam and water output levels.

As shown in FIG. 1, the time periods of "$t_s$" and "$t_w$" seconds, referred to as the steam and water "dead" times, respectively, represent the time it takes for the paper 18 to travel from the steam profiling bar 20 and moisture profiling bar 26, respectively, to the sensing assembly 30. These dead times include time delays introduced by the finite response times of the individual steam applicators 44 and water applicators 50. Thus, when the computer 34 orders a change in the amount of steam or water to be applied, the results of that change will not be seen by the sensing head 52 within the scanning assembly 30 until $t_s$ or $t_w$ seconds later, respectively.

The above-described process for measuring sheet moisture content and changing it through the appropriate application of more or less steam or water is done continuously for each individual slice 42 during the manufacturing process of the paper 18. This allows the moisture content profile of the sheet paper 18 to be tailored as desired simultaneously with its manufacture. Thus, when the reel 32 is removed, the paper 18 thereon contains the desired moisture in the desired profile (typically uniform, or "flat").

Figure 2A:
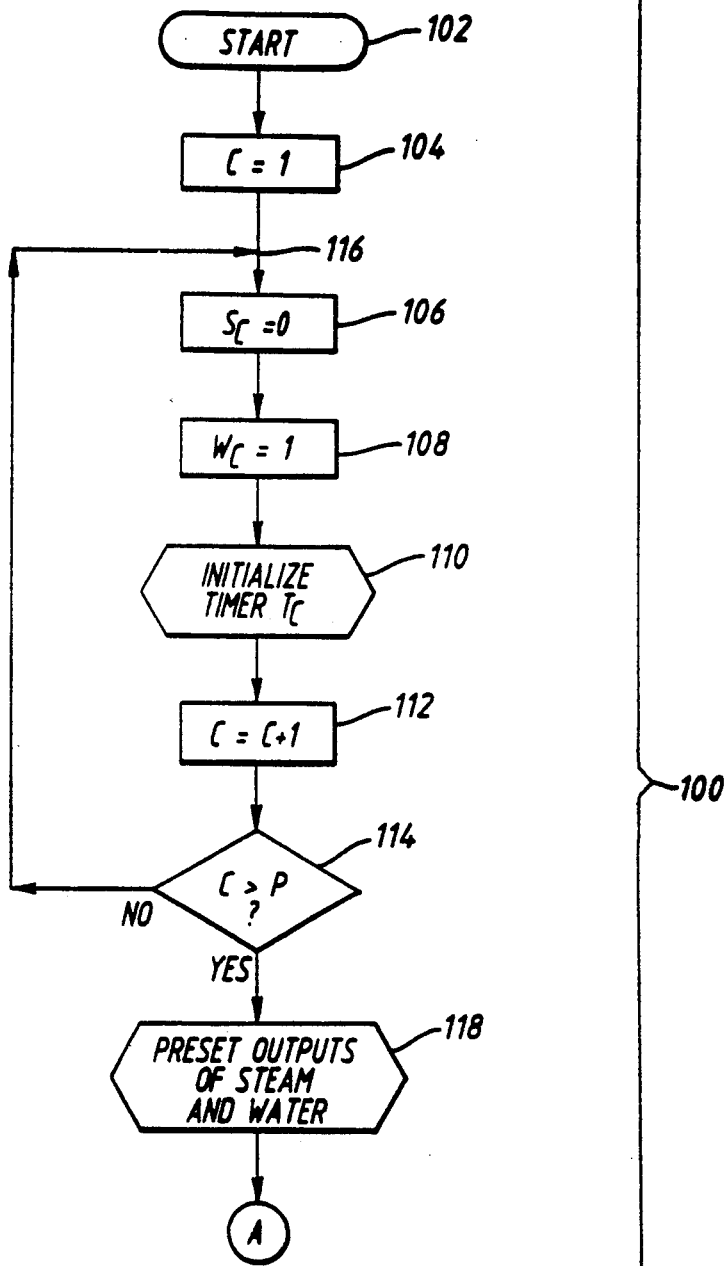
FIGS. 2A and 2B illustrate a flow chart for a representative computer program used in the present invention.
Figure 2B:
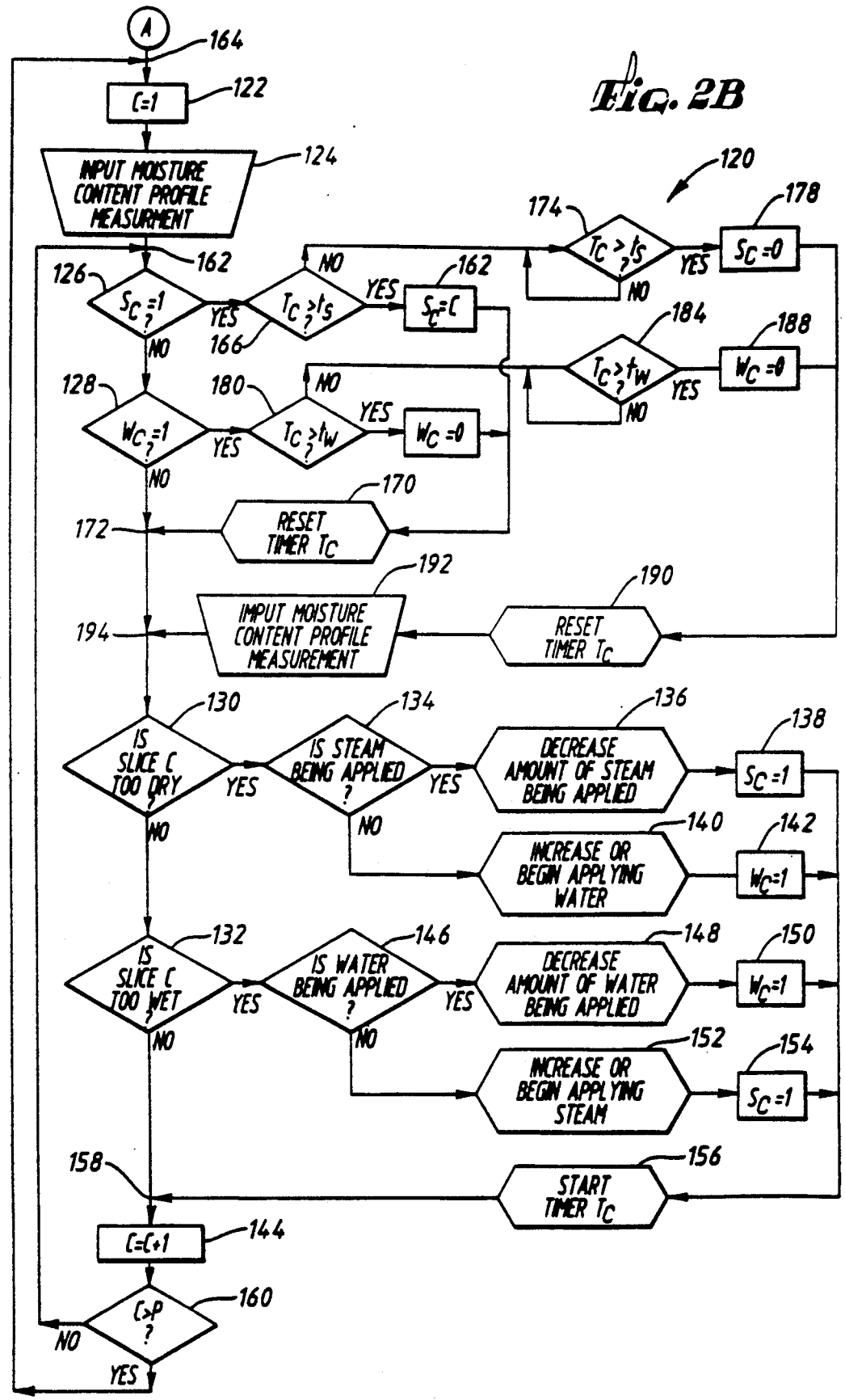

FIGS. 2A and 2B, a simplified flowchart for a representative computer program which may be used in the present invention, illustrate the logic representative of that associated with the measurement and analysis of the moisture content profile data, as well as the control of the application of steam and water by the computer 34, as described above. Other flowcharts, representing other logic, would also be within the scope of the present invention and within the abilities of those persons skilled in the art based upon the foregoing discussion.

FIG. 2A illustrates in flowchart form the initialization logic 100 representative of that logic which may be used to initialize a counter variable "C," status bits "$S_c$," "$W_c$," and an elapsed timer "$T_c$" used within the computer program used by the process control computer 34. The counter variable C is used to keep track of the "affected" slice 42, i.e., that slice 42 which is currently being analyzed and/or operated upon. The steam applicator status bit $S_c$ is used to indicate whether the steam applicator 44 associated with the affected slice 42 has been commanded by the computer 34 to begin, cease, increase or decrease its steam output. Likewise, the water applicator status bit $W_c$ is used to indicate whether the water applicator 50 associated with the affected slice 42 has been commanded by the computer 34 to begin, cease, increase or decrease its water output. The elapsed timer $T_c$ is used to indicate the time elapsing after the computer 34 has commanded the steam applicator 44 or water applicator 50 associated with the affected slice 42 to begin, cease, increase or decrease its steam or water output, respectively. This allows the computer 34 to know when sufficient time has elapsed, as compared to the steam and water dead times $t_s$, $t_w$, such that the moisture content data for the affected slice 42 being measured by the sensing head 52 and transmitted to the computer 34 represents the effect on that slice 42 caused by the modified application of steam or water.

Following the start 102 of the program, the program flow proceeds to block 104 where the counter variable C is initialized at "1," to indicate the first affected slice 42. The program flow then proceeds to blocks 106 and 108 where the steam and water applicator status bits associated with the first affected slice 42 are reset to logical zeros. Program flow then proceeds to block 110 where the elapsed timer $T_c$ associated with the first affected slice 42 is initialized to indicate zero elapsed time. Proceeding to block 112, the counter variable C is incremented to indicate the second affected slice 42. At block 114 the program compares the counter variable C to a preprogrammed number "P" which indicates the number of slices 42 to be analyzed and/or operated upon. If the counter variable C does not yet exceed the number P of slices 42, program flow returns to the point 116 to repeat the foregoing program steps of resetting the status bits $S_c$, $W_c$ and initializing the timer $T_c$ associated with the affected slice 42. Once the counter variable C exceeds the number P of slices 42, program flow proceeds to block 118 where, as described earlier, the outputs of the steam and water profiling bars 20, 26 are preset. Following this preset, program flow proceeds to the main operational portion 120 of the program, the representative logic for which is illustrated in FIG. 2B.

FIG. 2B illustrates in flowchart form the main operational logic 120 representative of that used in the main operational portion of the computer program used by the computer 34. Following the initialization sequence 100 described above for FIG. 2A, program flow proceeds to block 122 where the counter variable C is re-initialized at "1" to again indicate the first affected slice 42. Program flow then proceeds to block 124 where the moisture content profile data measured by the sensing head 52, as described earlier, is inputted to the computer 34. The first time through, program flow proceeds directly through blocks 126 and 128 since the status bits $S_c$, $W_c$ had just been reset to logical zeros in the initialization sequence 100 described above for FIG. 2A. At block 130, the moisture content data for the affected slice 42 is analyzed to see whether the affected slice 42 is too dry. If not, the program flow proceeds to block 132. However, if the affected slice 42 is too dry, the program flow proceeds to block 134 where it is determined whether steam is being applied to the affected slice 42. If steam is being applied, program flow proceeds to block 136 where the amount of steam being applied by the associated steam applicator 44 is reduced by a predetermined incremental amount, as described earlier, and the corresponding steam applicator status bit $S_c$ is set to a logical one, as shown in block 138. If, on the other hand, steam is not being applied, program flow proceeds to block 140 where the associated water applicator 50 is instructed to begin or increase its application of water to the affected slice 42, and the associated water applicator status bit $W_c$ is set to a logical one, as shown in block 142.

If at block 130 it was determined that the affected slice 42 was not too dry, the program flow proceeds to block 132 where it is determined whether the affected slice 42 is too wet. If not, program flow proceeds to block 144 where the counter variable C is incremented by one. If, however, the affected slice 42 is too wet, program flow proceeds to block 146 where it is determined whether water is being applied by the associated water applicator 50. If water is already being applied, program flow proceeds to block 148 where the associated water applicator 50 is instructed to decrease the amount of water it is applying to the affected slice 42, and the associated water applicator status bit $W_c$ is set to a logical one, as indicated in block 150. If, on the other hand, no water is being applied, program flow proceeds to block 152 where the associated steam applicator 44 is instructed to begin or increase the amount of steam it is applying to the affected slice 42, and the associated steam applicator status bit $S_c$ is set to a logical one, as indicated in block 154.

Following the logical setting of the status bits $S_c$, $W_c$ in blocks 138, 142, 150, 154, program flow proceeds to block 156 where the associated elapsed timer $T_c$ is started. Program flow then proceeds to point 158 and block 144 where, as stated above, the counter variable C is incremented by one.

Following its incrementation, the counter variable C is compared to the preprogrammed number P of slices 42 in program block 160. Still being the first time through the program and the counter variable C only indicating the second affected slice 42, the program flow will proceed to point 162 and the foregoing steps will be repeated. Once the counter variable C has been incremented in block 144 beyond the number P of slices 42, program flow will proceed from block 160 to point 164 where full, normal program operation will begin.

Once full, normal program operation begins, the counter variable C is once again initialized at "1" to indicate the first affected slice 42 (block 122) and the moisture content profile data measured by the sensing head 52 is re-inputted (block 124). Program flow proceeds to block 126 where the steam applicator status bit $S_c$ is checked. If a logical zero (i.e., associated steam applicator 44 had not recently been instructed to modify its steam output), program flow proceeds to block 128. However, if a logical one (i.e., associated steam applicator 44 recently instructed to modify its steam output), program flow proceeds to block 166 where the associated elapsed timer $T_c$ is checked to see if the time elapsed since the associated steam applicator status bit $S_c$ was set to a logical one exceeds the steam applicator dead time $t_s$. If so, the status bit $S_c$ is reset to a logical zero (block 168) and the elapsed timer $T_c$ is re-initialized (block 170), and program flow proceeds to point 172. If, on the other hand, the elapsed time does not exceed the steam applicator dead time $t_s$, program flow proceeds to block 174 where the program enters a waiting mode, i.e., program flow stays within a loop 176 until sufficient time has elapsed. Once the elapsed time, as indicated by the elapsed timer $T_c$, has exceeded the steam applicator dead time $t_s$, the associated steam applicator status bit $S_c$ is reset to a logical zero (block 178).

In block 128, the program checks the water applicator status bit $W_c$ associated with the affected slice 42. If a logical zero (i.e., associated water applicator 50 had not recently been instructed to modify its water output), program flow proceeds to block 130. However, if a logical one (i.e., associated water applicator 50 recently instructed to modify its water output), the elapsed timer $T_c$ is checked to see if the time elapsed since the logical setting of the water applicator status bit $W_c$ exceeds the water applicator dead time $t_w$ (block 180). If so, the water applicator status bit $W_c$ is reset to a logical zero (block 182), the elapsed timer $T_c$ is re-initialized (block 170) and program flow proceeds to point 172. If, on the other hand, the elapsed time does not exceed the water applicator dead time $t_w$, program flow proceeds to block 184 where the program idles in a loop 186 until sufficient time has elapsed. Once the water applicator dead time $t_w$ has been exceeded, the associated water applicator status bit $W_c$ is reset to a logical zero (block 188).

After the appropriate, associated status bit $S_c$, $W_c$ has been reset to a logical zero in block 178 or 188, the elapsed timer $T_c$ is re-initialized (block 190) and new moisture content profile data is inputted (block 192). It is necessary for new input moisture content profile data to be entered at this point because, as described above, the program has had to wait for sufficient time to elapse such that the effects of the modification of steam or water application may be measured by the sensing head 52. Once this new moisture content profile data has been inputted, program flow proceeds to point 194 and on to block 130.

Once program flow has proceeded to blocks 130 and 132, the program flow described above for block 130 through point 158 is repeated. Until the counter variable C exceeds the preprogrammed number P of slices 42, as determined in block 160, the foregoing program flow beginning with block 126 is repeated. Once the counter variable C exceeds the number P of slices 42, program flow beginning with block 122 is repeated, i.e., analysis and treatment by steam or water of the slices 42 is repeated, beginning with the first affected slice 42.

The foregoing description is to be considered as merely exemplary and not limiting in any way with respect to the present invention and any embodiment thereof. Thus, the present invention is not necessarily limited to the control of moisture in paper, but may extend, for example, to the control of any physical property or characteristic in any material which can be affected in opposing senses with two spaced devices and sensed by a single sensor downstream of the two spaced devices. Therefore, the specific scope and subject matter of the present invention is to be determined according to the claims.

What is claimed is:

1. An apparatus for sensing and controlling a physical characteristic of a material, including a pathway for moving the material from an upstream position to a downstream position along the pathway, the apparatus comprising:
   a first device, disposed at a first location along the pathway, for affecting a physical characteristic of the material when the first device is applied;
   a second device, disposed at a second location along the pathway, for affecting the physical characteristic when the second device is applied in a manner tending to counteract the effect of the first device;
   a sensor, disposed downstream along the pathway from the first and second devices, for sensing the physical characteristic and generating a signal indicative thereof; and
   a controller, coupled to the first and second devices and to the sensor, for adjusting the first and second device in accordance with the signal, wherein the first device is only applied with respect to a location of the material when the second device is not and the second device is only applied with respect to the location of the material when the first device is not such that the first and second devices do not affect the physical characteristic of the material at the same location.

2. An apparatus as in claim 1, wherein the second location is spaced along the pathway in the machine direction from the first location.

3. An apparatus as in claim 1, wherein the material is paper sheet and the physical characteristic is sheet moisture content.

4. An apparatus as in claim 3, wherein the first device includes a steam applicator for applying steam to a first surface of the sheet.

5. An apparatus as in claim 4, wherein the first device further includes a vacuum device for applying a vacuum to a second surface of the sheet opposite the first surface.

6. An apparatus as in claim 3, wherein the second device includes a water applicator for applying water to a surface of the sheet.

7. An apparatus as in claim 3, wherein the sensor includes a moisture detector for sensing the moisture content of the sheet.

8. An apparatus for controlling a physical characteristic of material moving from an upstream position to a downstream position along a pathway, the apparatus comprising:
   a first device, disposed at a first location along the pathway, for affecting a physical characteristic of the material when the first device is applied;
   a second device, disposed at a second location along the pathway, for affecting the physical characteristic when the second device is applied in a manner tending to counteract the effect of the first device;
   a sensor, disposed downstream along the pathway from the first and second devices, for sensing the physical characteristic and generating a signal indicative thereof; and
   a controller, coupled to the first and second devices and to the sensor, for adjusting the first and second device in accordance with the signal so that either the first device or the second device is applied.

9. An apparatus for controlling a physical characteristic of material moving from an upstream to a downstream position along a pathway, including a first device, disposed at a first location along the pathway, for affecting a physical characteristic of the material when the first device is applied and a second device, disposed at a second location along the pathway, for affecting the physical characteristic when the second device is applied in a manner tending to counteract the effect of the first device, the apparatus comprising:
   a sensor, disposed downstream along the pathway from the first and second devices, for sensing the physical characteristic and generating a signal indicative thereof;
   a controller for adjusting the first and second device in accordance with a signal such that the first and second device do not affect the physical characteristic at the same location of the material;
   and wherein said first device affects the physical characteristic of the material at a plurality of cross-directional sections when the first device is applied; and
   said second device affects the physical characteristic at the plurality of cross-directional sections when the second device is applied in a manner tending to counteract the effect of the first device.

10. An apparatus as in claim 9, wherein the physical characteristic being controlled is sheet moisture.

11. An apparatus as in claim 9, wherein the first device includes a steam applicator for applying steam to a first surface of the material.

12. An apparatus as in claim 11, wherein the first device further includes a vacuum device for applying a vacuum to a second surface of the material opposite the first surface.

13. An apparatus as in claim 9, wherein the second device includes a water applicator for applying water to a surface of the material.

14. An apparatus as in claim 9, wherein the sensor is a moisture detector for sensing the moisture of the material.

* * * * *